(12) United States Patent
Widenhouse et al.

(10) Patent No.: US 8,753,338 B2
(45) Date of Patent: Jun. 17, 2014

(54) ELECTROSURGICAL INSTRUMENT EMPLOYING A THERMAL MANAGEMENT SYSTEM

(75) Inventors: Tamara Widenhouse, Clarksville, OH (US); Frederick E. Shelton, IV, Hillsboro, OH (US); Craig N. Faller, Milford, OH (US); James R. Giordano, Milford, OH (US); Matthew C. Miller, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1042 days.

(21) Appl. No.: 12/797,853

(22) Filed: Jun. 10, 2010

(65) Prior Publication Data

US 2011/0306972 A1    Dec. 15, 2011

(51) Int. Cl.
*A61B 18/14*    (2006.01)
(52) U.S. Cl.
USPC .................................. 606/45; 606/41; 606/51
(58) Field of Classification Search
USPC ..................................... 606/45–52, 205–207
See application file for complete search history.

(56) References Cited

U.S. PATENT DOCUMENTS

| | | | |
|---|---|---|---|
| 2,366,274 A | 1/1945 | Luth et al. | |
| 2,458,152 A | 1/1949 | Eakins | |
| 2,510,693 A | 6/1950 | Green | |
| 3,166,971 A | 1/1965 | Stoecker | |
| 3,580,841 A | 5/1971 | Cadotte et al. | |
| 3,703,651 A | 11/1972 | Blowers | |
| 4,005,714 A | 2/1977 | Hiltebrandt | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,545,926 A | 10/1985 | Fouts, Jr. et al. | |
| 4,550,870 A | 11/1985 | Krumme et al. | |
| 4,582,236 A | 4/1986 | Hirose | |

(Continued)

FOREIGN PATENT DOCUMENTS

| | | |
|---|---|---|
| DE | 29623113 U1 | 10/1997 |
| DE | 20004812 U1 | 9/2000 |

(Continued)

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.

(Continued)

*Primary Examiner* — Linda Dvorak
*Assistant Examiner* — Amanda Scott

(57) ABSTRACT

An electrosurgical surgical instrument can comprise a handle and an end effector, wherein the end effector can comprise first and second jaws which can be opened and closed in order to capture tissue therebetween. In various embodiments, the first and second jaws can comprise one or more electrodes configured to apply a voltage across the tissue thereby causing current to flow through the tissue and, as a result, generate heat within the tissue. The surgical instrument can further comprise a fluid circulatory system embedded within at least a portion the end effector wherein, in at least one embodiment, the fluid can be dispensed from the fluid circulatory system and onto the jaws of the end effector and/or the tissue positioned between the jaws.

23 Claims, 8 Drawing Sheets

(56) References Cited

U.S. PATENT DOCUMENTS

| | | |
|---|---|---|
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A | 3/1993 | Abele et al. |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,618,307 A | 4/1997 | Donlon et al. |
| 5,624,452 A | 4/1997 | Yates |
| 5,647,871 A * | 7/1997 | Levine et al. .............. 606/45 |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,241,294 B2 | 7/2007 | Reschke |
| 7,252,667 B2 | 8/2007 | Moses et al. |
| 7,267,685 B2 | 9/2007 | Butaric et al. |
| 7,287,682 B1 | 10/2007 | Ezzat et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |

(56) References Cited

U.S. PATENT DOCUMENTS

| | | |
|---|---|---|
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,020,743 B2 | 9/2011 | Shelton, IV |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,282,669 B2 | 10/2012 | Gerber et al. |
| 8,298,232 B2 | 10/2012 | Unger |
| 8,323,310 B2 | 12/2012 | Kingsley |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1* | 8/2003 | Phan et al. ............... 606/41 |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0033278 A1 | 2/2005 | McClurken et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0138003 A1 | 5/2009 | Deville et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0136353 A1 | 5/2012 | Romero |
| 2012/0150176 A1 | 6/2012 | Weizman |
| 2013/0023875 A1 | 1/2013 | Harris et al. |
| 2013/0053831 A1 | 2/2013 | Johnson et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |

(56) References Cited

FOREIGN PATENT DOCUMENTS

| | | |
|---|---|---|
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/089717 A1 | 7/2011 |
| WO | WO 03/001986 A2 | 1/2013 |

OTHER PUBLICATIONS

International Preliminary Report on Patentability for PCT/US2011/039713, Dec. 10, 2012 (5 pages).
International Search Report for PCT/US2011/039713, Sep. 19, 2011 (5 pages).
U.S. Appl. No. 13/221,410, filed Aug. 30, 2011.
U.S. Appl. No. 13/189,169, filed Jul. 22, 2011.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.

(56) References Cited

OTHER PUBLICATIONS

U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
U.S. Appl. No. 12/797,844, filed Jun. 10, 2010.
U.S. Appl. No. 12/797,861, filed Jun. 10, 2010.
U.S. Appl. No. 12/797,866, filed Jun. 10, 2010.

* cited by examiner

ELECTROSURGICAL INSTRUMENT EMPLOYING A THERMAL MANAGEMENT SYSTEM

BACKGROUND

1. Field of the Invention

The present invention relates to medical devices and methods. More particularly, the present invention relates to electrosurgical instruments and methods for sealing and transecting tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency (Rf) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In at least one form, a surgical instrument can comprise a handle, a fluid inlet, a fluid outlet, a first conductor configured to be electrically coupled to a power source, and a second conductor. The surgical instrument can further comprise an end effector including a first jaw and a second jaw, wherein one of the first jaw and the second jaw is movable relative to the other of the first jaw and the second jaw between an open position and a closed position to capture tissue therebetween. The end effector can further comprise a first electrode electrically coupled with the first conductor and a second electrode electrically coupled with the second conductor. The surgical instrument can further comprise a fluid conveying circuit comprising a first fluid passage in fluid communication with the fluid inlet and a second fluid passage in fluid communication with the first fluid passage and the fluid outlet. In various embodiments, at least one of the first fluid passage and the second fluid passage is configured to rupture such that fluid flowing through the fluid conveying circuit can flow onto the tissue captured between the first jaw and the second jaw.

In at least one form, a surgical instrument can comprise a handle comprising a trigger and a switch, and a shaft extending from the handle, wherein the shaft comprises a first conductor configured to be electrically coupled with a power source upon an actuation of the switch, a second conductor, and a drive member operably coupled with the trigger. The surgical instrument can further comprise an end effector extending from the shaft comprising a first jaw, a second jaw, wherein one of the first jaw and the second jaw is movable relative to the other of the first jaw and the second jaw between an open position and a closed position to capture tissue therebetween, a first electrode electrically coupled with the first conductor, a second electrode electrically coupled with the second conductor, and a cutting member operably coupled with the drive member, wherein an actuation of the trigger is configured to move the cutting member between a proximal position and a distal position. The surgical instrument can further comprise a fluid conveying circuit including a first fluid passage in fluid communication with the fluid inlet and a second fluid passage in fluid communication with the first fluid passage and the fluid outlet. In various embodiments, at least one of the first fluid passage and the second fluid passage is configured to rupture such that fluid flowing through the fluid conveying circuit can flow onto the tissue captured between the first jaw and the second jaw.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
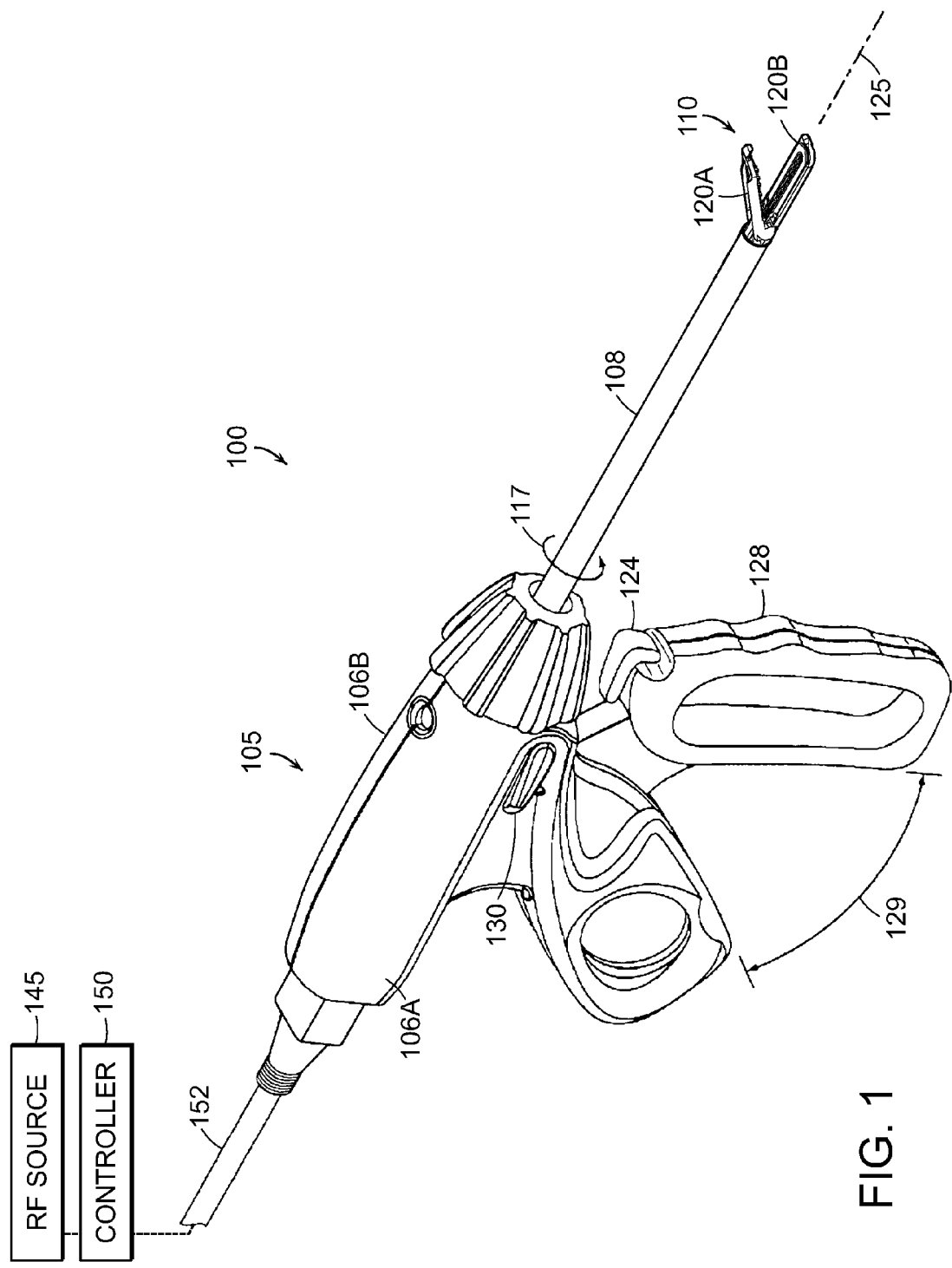
FIG. 1 is a perspective view of an electrosurgical instrument.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

The entire disclosures of the following co-owned non-provisional United States patent applications filed on even date herewith are hereby incorporated by reference herein:

U.S. patent application Ser. No. 12/797,866, entitled HEAT MANAGEMENT CONFIGURATIONS FOR CONTROLLING HEAT DISSIPATION FROM ELECTROSURGICAL INSTRUMENTS, now U.S. Patent Application Publication No. 2011/0306968;

U.S. patent application Ser. No. 12/797,861, entitled COOLING CONFIGURATIONS FOR ELECTROSURGICAL INSTRUMENTS, now U.S. Patent Application Publication No. 2011/0306967; and U.S. patent application Ser. No. 12/797,844, entitled ELECTROSURGICAL INSTRUMENT COMPRISING SEQUENTIALLY ACTIVATED ELECTRODES, now U.S. Patent Application Publication No. 2011/0306973.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures adapted for transecting captured tissue between the jaws and for contemporaneously welding the captured tissue margins with controlled application of RF energy. The jaw structures can comprise a scoring element which can cut or score tissue independently of the tissue capturing and welding functions of the jaw structures. The jaw structures can comprise first and second opposing jaws that carry positive temperature coefficient (PTC) bodies for modulating RF energy delivery to the engaged tissue.

A surgical instrument can be configured to supply energy, such as electrical energy, ultrasonic energy, and/or heat energy, for example, to the tissue of a patient. For example, various embodiments disclosed herein can comprise electrosurgical jaw structures adapted for transecting captured tissue positioned between the jaws and for contemporaneously welding margins of the captured tissue with the controlled application of RF energy, for example. Referring now to FIG. 1, an electrosurgical instrument 100 is shown. Electrosurgical instrument 100 can comprise a proximal handle 105, a distal working end or end effector 110, and an introducer or elongate shaft 108 disposed therebetween. End effector 110 may comprise a set of openable and closeable jaws, such as an upper first jaw 120A and a lower second jaw 120B, for example, which can comprise straight and/or curved configurations. First jaw 120A and second jaw 120B may each comprise an elongate slot or channel therein disposed within their respective middle portions along axis 125, for example. As described in greater detail below, first jaw 120A and second jaw 120B may be coupled to an electrical source or RF source 145 and a controller 150 through electrical leads in cable 152. Controller 150 may be used to activate electrical source 145. In various embodiments, the electrical source 145 may comprise an RF source, an ultrasonic source, a direct current source, and/or any other suitable type of electrical energy source, for example.

Figure 2:
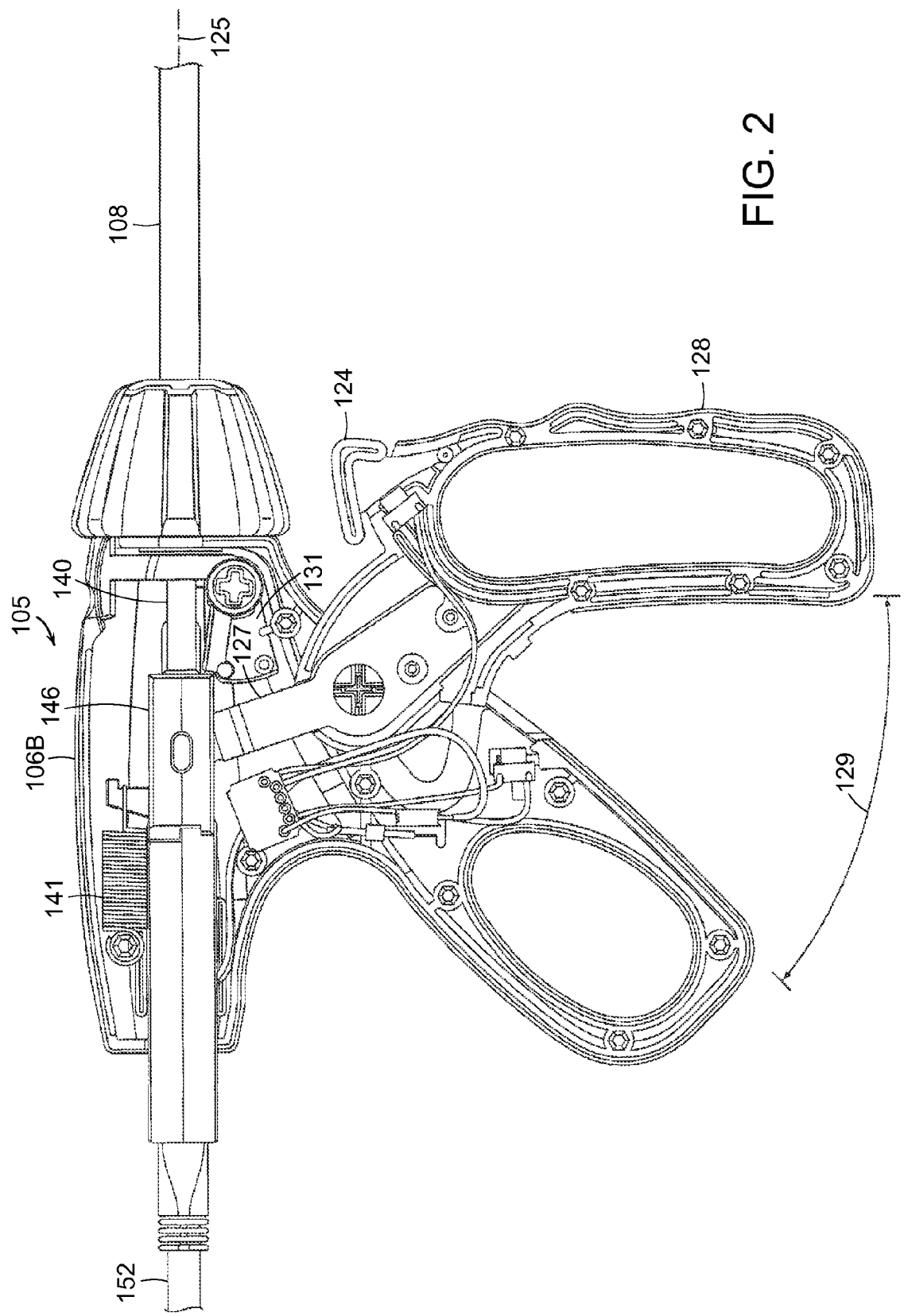
FIG. 2 is a side view of a handle of the surgical instrument of FIG. 1 with a half of a handle body removed to illustrate some of the components therein.

Moving now to FIG. 2, a side view of the handle 105 is shown with a first handle body 106A (see FIG. 1) removed to illustrate some of the components within second handle body 106B. Handle 105 may comprise a lever arm, or trigger, 128 which may be pulled along a path 129. Lever arm 128 may be coupled to a movable cutting member disposed within elongate shaft 108 by a shuttle 146 operably engaged to an extension 127 of lever arm 128. The shuttle 146 may further be connected to a biasing device, such as spring 141, for example, which may also be connected to the second handle body 106B, wherein the spring 141 can be configured to bias the shuttle 146 and thus the cutting member in a proximal direction. When the cutting member is in a proximal position, the jaws 120A and 120B can be urged into an open configuration as seen in FIG. 1 by a jaw spring disposed between a portion of the jaws 120A and 120B, for example. Also, referring to FIGS. 1 and 2, a locking member 131 (see FIG. 2) may be moved by a locking switch 130 (see FIG. 1) between a locked position in which the shuttle 146 can be prevented from moving distally and an unlocked position in which the shuttle 146 may be allowed to freely move in the distal direction toward the elongate shaft 108. The handle 105 can be any type of pistol-grip or other type of handle known in the art that is configured to carry actuator levers, triggers and/or sliders for actuating the first jaw 120A. Elongate shaft 108 may have a cylindrical and/or rectangular cross-section and can comprise a thin-wall tubular sleeve that extends from handle 105. Elongate shaft 108 may include a bore extending therethrough for carrying actuator mechanisms configured to actuate the jaws and/or for carrying electrical leads configured to conduct electrical energy to electrosurgical components of end effector 110.

End effector 110 may be adapted for capturing, welding and transecting tissue. In various embodiments, at least one of first jaw 120A and second jaw 120B may be closed to capture or engage tissue therebetween. First jaw 120A and second jaw 120B may also apply compression to the tissue. Elongate shaft 108, along with first jaw 120A and second jaw 120B, can be rotated a full 360° degrees, as shown by arrow 117, relative to handle 105 through one or more rotary contacts, for example. First jaw 120A and second jaw 120B can remain openable and/or closeable while rotated. Referring now to FIG. 1, end effector 110 may be coupled to electrical source 145 and controller 150. Controller 150 can regulate the electrical energy delivered by electrical source 145 which in turn delivers electrosurgical energy to electrodes within the jaws 120A, 120B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. As described in greater detail below, the electrodes of the jaw members may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 3:
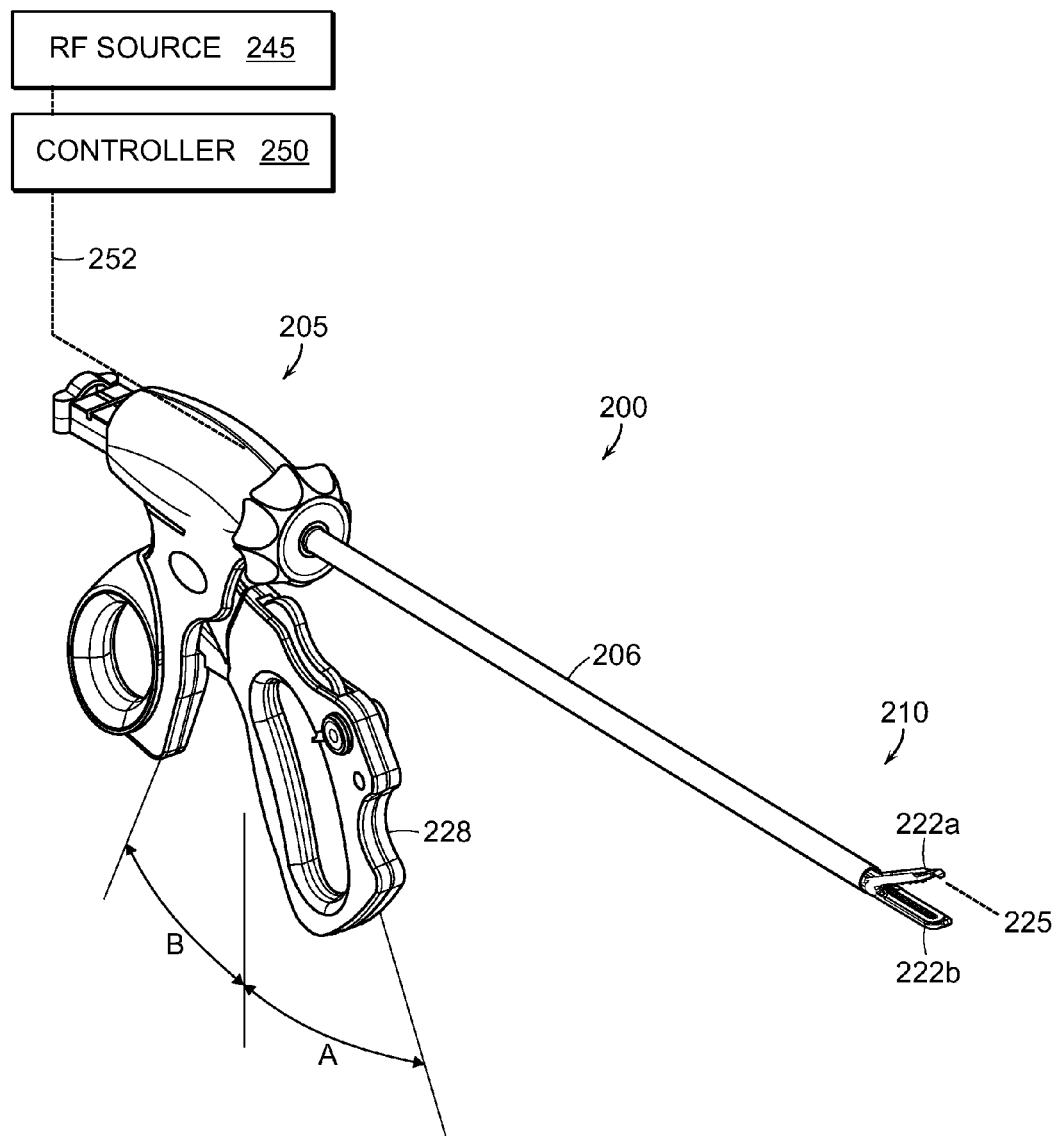
FIG. 3 is a perspective view of an electrosurgical instrument.
Figure 4A:
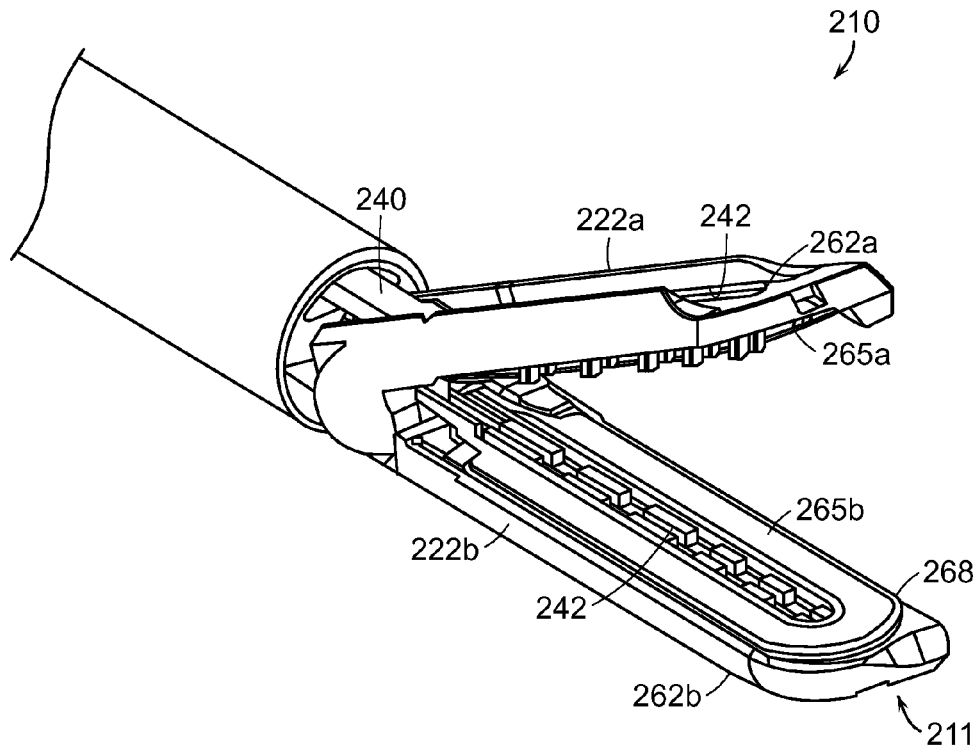
FIG. 4A illustrates an end effector of an electrosurgical instrument in an open configuration.
Figure 4B:
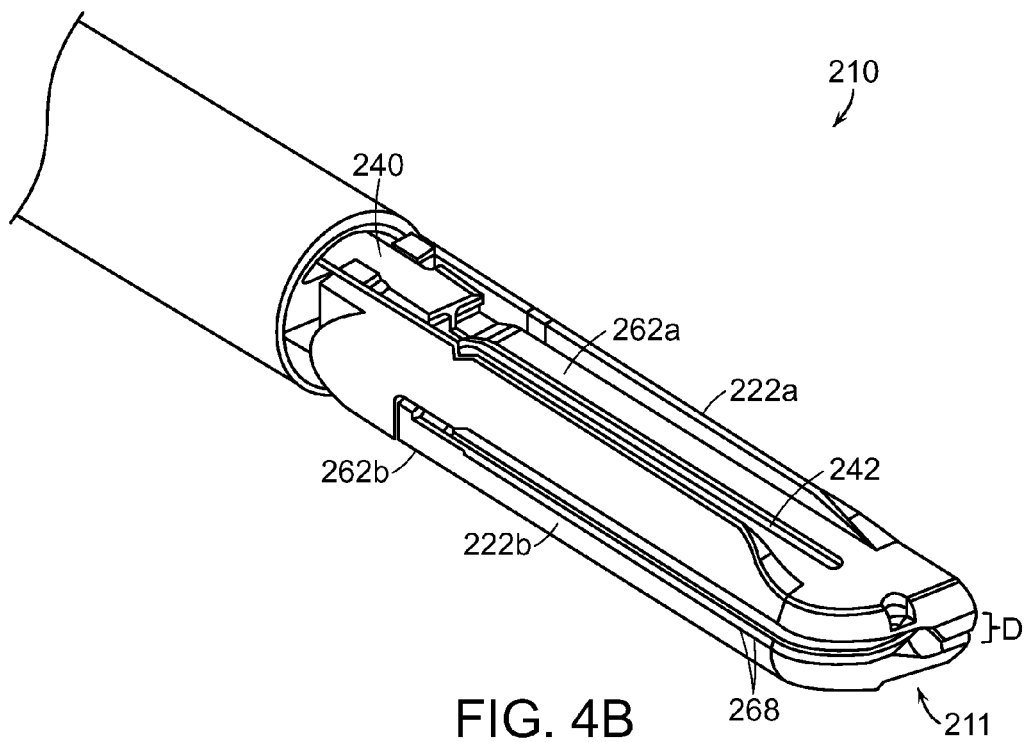
FIG. 4B illustrates the end effector of FIG. 4A in a closed configuration.

FIG. 3 illustrates an electrosurgical instrument 200 comprising a handle end 205, a shaft, or introducer, 206, and an end effector, or working end, 210. Shaft 206 can comprise any suitable cross-section, such as a cylindrical and/or rectangular cross-section, for example, and can comprise a tubular sleeve that extends from handle 205. End effector 210 can extend from shaft 206 and may be adapted for welding and transecting tissue. In various embodiments, end effector 210 can comprise an openable and closeable jaw assembly which can, in various embodiments, comprise straight, curved, and/or any other suitably configured jaws. In various embodiments, the end effector 210 can comprise a first jaw 222a and a second jaw 222b, wherein at least one of the jaws 222a and 222b can move relative to the other. In at least one embodiment, the first jaw 222a can be pivoted about an axis relative to the second jaw 222b in order close onto, capture, and/or engage tissue positioned between the jaws and apply a compression force or pressure thereto. In various embodiments, the handle 205 can comprise a lever arm, or trigger, 228 adapted to actuate a translatable member 240 (see FIG. 4A). More particularly, in at least one embodiment, the lever arm 228 can be actuated in order to move member 240 distally toward the distal end 211 of end effector 210 and, when member 240 is advanced distally, member 240 can contact first jaw 222a and move it downwardly toward second jaw 222b, as illustrated in FIG. 4B. In at least one embodiment, the translatable member 240 can comprise a proximal rack portion and the lever arm 228 can comprise a plurality of gear teeth which can be configured to drive the proximal rack portion of translatable member 240 distally. In certain embodiments, rotation of the lever arm 228 in the opposite direction can drive the translatable member 240 proximally.

Figure 4C:
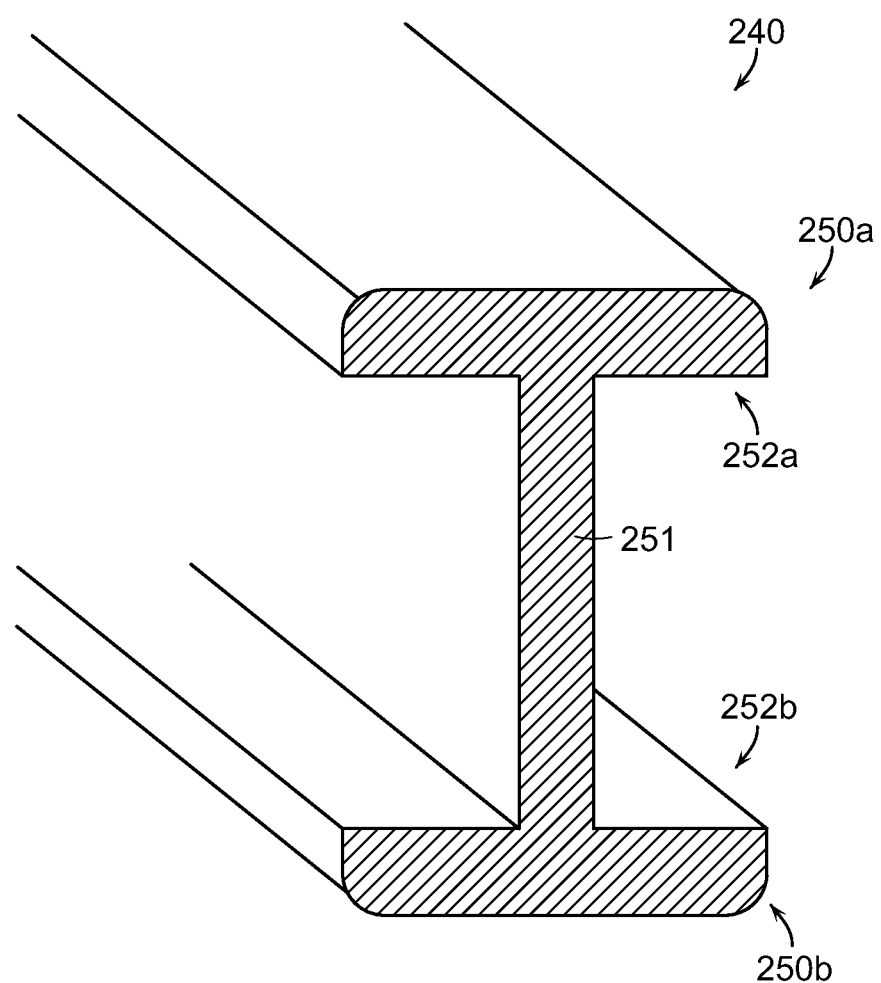
FIG. 4C is a sectional view of a translatable member shaped like an I-beam which is configured to close the end effector of the surgical instrument of FIG. 3.

As described above, the translatable member 240 can be configured to contact first jaw 222a and pivot jaw 222a toward second jaw 222b. In various embodiments, referring now to FIGS. 4A-4C, the distal end of reciprocating member 240 can comprise a flanged "I"-beam configured to slide within a channel 242 in the jaws 222a and 222b. Referring primarily to FIG. 4C, the I-beam portion of member 240 can comprise an upper flange 250a, a lower flange 250b, and a center, or intermediate, portion 251 connecting the flanges 250a and 250b. In at least one embodiment, the flanges 250a and 250b and the center portion 251 can define "c"-shaped channels on the opposite sides of member 240. In any event, in various embodiments, the flanges 250a and 250b can define inner cam surfaces 252a and 252b, respectively, for slidably engaging outward-facing surfaces 262a and 262b of jaws 222a and 222b, respectively. More particularly, the inner cam surface 252a can comprise a suitable profile configured to slidably engage the outer surface 262a of first jaw 222a and, similarly, the inner cam surface 252b can comprise a suitable profile configured to slidably engage the outer surface 262b of second jaw 222b such that, as translatable member 240 is advanced distally, the cam surfaces 252a and 252b can co-operate to cam first jaw member 222a toward second jaw member 222b and configure the end effector 210 in a closed configuration. As seen in FIG. 4B, jaws 222a and 222b can define a gap, or dimension, D between the first and second electrodes 265a and 265b of jaws 222a and 222b, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

As discussed above, the translatable member 240 can be at least partially advanced in order to move the first jaw 222a toward the second jaw 222b. Thereafter, the movable member 240 can be advanced further distally in order to transect the tissue positioned between the first jaw 222a and the second jaw 222b. In certain embodiments, the distal, or leading, end of the I-beam portion of member 240 can comprise cutting member including a sharp, or knife, edge which can be configured to incise the tissue. Before, during, and/or after the member 240 is advanced through the tissue, electrical current can be supplied to the electrodes in the first and second jaw members in order to weld the tissue, as described in greater detail further below. In various circumstances, the operation of the trigger 228 can advance the knife edge of the cutting member 240 along axis 225 to the very distal end of slot or channel 242. After the cutting member 240 has been sufficiently advanced, the trigger 228 can be released and moved into its original, or unactuated, position in order to retract the cutting member 240 and allow first jaw 222a to move into is open position again. In at least one such embodiment, the surgical instrument can comprise a jaw spring configured to bias the first jaw 222a into its open position and, in addition, a trigger spring configured to bias the trigger 228 into its unactuated position.

In various embodiments, further to the above, the surgical instrument can comprise a first conductor, such as an insulated wire, for example, which can be operably coupled with the first electrode 265a in first jaw member 222a and, in addition, a second conductor, such as an insulated wire, for example, which can be operably coupled with the second electrode 265b in second jaw member 222b. In at least one embodiment, referring again to FIG. 3, the first and second conductors can extend through shaft 206 between an electrical connector in handle 205 and the electrodes 265a and 265b in the end effector 210. In use, the first and second conductors can be operably coupled to electrical source 245 and controller 250 by electrical leads in cable 252 in order for the electrodes 265a and 265b to function as paired bi-polar electrodes with a positive polarity (+) and a negative polarity (−). More particularly, in at least one embodiment, one of the first and second electrodes 265a and 265b can be operably coupled with a positive (+) voltage terminal of electrical source 245 and the other of the first and second electrodes 265a and 265b can be electrically coupled with the negative voltage (−) terminal of electrical source 245. Owing to the opposite polarities of electrodes 265a and 265b, current can flow through the tissue positioned between the electrodes 265a and 265b and heat the tissue to a desired temperature. In certain embodiments, the cutting member 240 can act as an electrode when it is electrically coupled to a positive terminal or negative terminal of the source 245, and/or any suitable ground.

Figure 5:
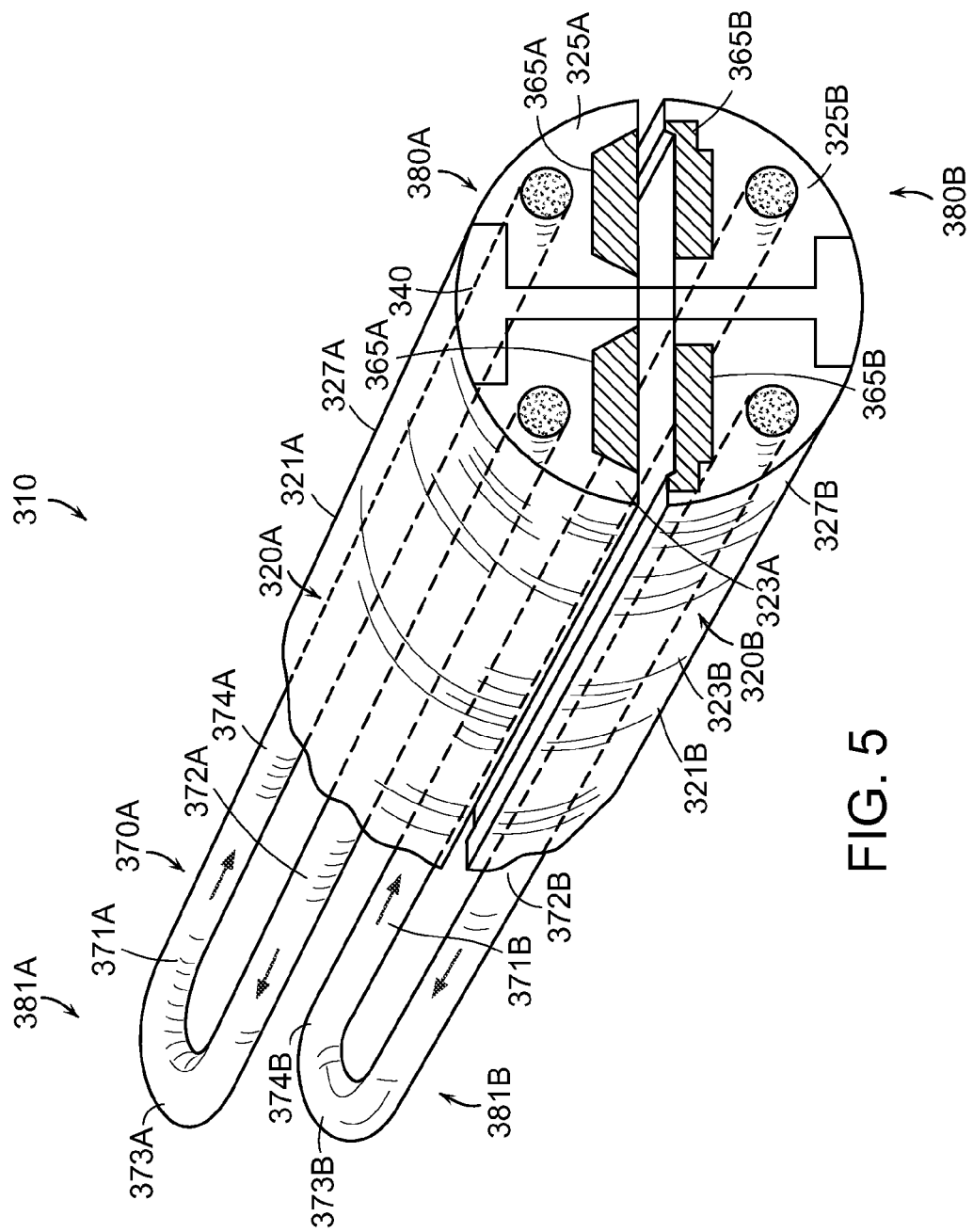
FIG. 5 is a cross-sectional perspective view of an end effector of an electrosurgical instrument including fluid-conveying conduits extending through and embedded within first and second jaws of the end effector, illustrated with portions of the end effector removed.

In use, as described above, current flowing through the electrodes and the tissue positioned between the electrodes can generate thermal energy. In various circumstances, an excessive quantity of thermal energy can be created and, in some circumstances, the thermal energy can spread laterally away from the end effector into tissue positioned adjacent to the end effector. In various embodiments disclosed herein, a surgical instrument can comprise a system for removing thermal energy from the end effector, the tissue being treated by the end effector, and/or the tissue surrounding the end effector, for example. In certain embodiments, referring now to FIG. 5, a surgical instrument can comprise an end effector 310 including a first jaw 320A and a second jaw 320B wherein, similar to the above, at least one of jaws 320A, 320B can be moved relative to the other in order to capture tissue therebetween. Also similar to the above, the first jaw 320A can comprise first electrodes 365A and the second jaw 320B can comprise second electrodes 365B wherein current can flow between the electrodes 365A and 365B. In various embodiments, the first jaw 320A can comprise a jaw body 321A and, in addition, a fluid-circulating circuit, or passage, 370A extending through the jaw body 321A. In certain embodiments, the fluid-circulating circuit 370A can comprise a continuous conduit 371A extending between a proximal end 380A of first jaw member 320A and a distal end 381A of the first jaw member 320A. In various embodiments, the conduit 371A can extend along a first side 323A of first jaw 320A, through the distal end 381A of first jaw 320A, and along a second side 325A of first jaw 320A. In various embodiments, the conduit 371A can be located adjacent to the outer perimeter of 327A of first jaw 320A, for example. In at least one embodiment, the conduit 371A can be positioned radially outwardly with respect to the first electrodes 365A. In certain embodiments, the geometry of conduit 371A can parallel the geometry of the electrodes 365A. More particularly, in at least one embodiment, the conduit 371A can comprise a first portion 372A which extends longitudinally along an electrode 365A within the first side 323A of jaw member 320A, a distal end portion 373A which extends to and/or around the distal end of the electrode 365A, and a second portion 374A which extends longitudinally along another electrode 365A positioned on the opposite, or second, side 325A of jaw member 320A.

In various embodiments, referring again to FIG. 5, the second jaw 320B can comprise a jaw body 321B and, in addition, a second fluid-circulating circuit 370B extending through the jaw body 321B. In certain embodiments, the fluid-circulating circuit 370B can comprise a continuous conduit 371B extending between a proximal end 380B of second jaw member 320B and a distal end 381B of the second jaw member 320B. In various embodiments, the second conduit 371B can extend along a first side 323B of second jaw 320B, through the distal end 381B of second jaw 320B, and along a second side 325B of second jaw 320B. In various embodiments, the conduit 371B can be located adjacent to the outer perimeter of 327B of second jaw 320B, for example. In at least one embodiment, the conduit 371B can be positioned radially outwardly with respect to the second electrodes 365B. In certain embodiments, the geometry of conduit 371B can parallel the geometry of the electrodes 365B. More particularly, in at least one embodiment, the conduit 371B can comprise a first portion 372B which extends longitudinally along an electrode 365B within the first side 323B of jaw member 320B, a distal end portion 373B which extends to and/or around the distal end of the electrode 365B, and a second portion 374B which extends longitudinally along another electrode 365B positioned on the opposite, or second, side 325B of jaw member 320B. Referring again to FIG. 5, the first portions 372A, 372B of fluid circuits 370A, 370B extend along a first side of cutting member 340 while the second portions 374A, 374B extend along an opposite, or second side, of cutting member 340. Similar to the above, the cutting member 340 can be moved between a proximal position within the proximal ends 380A, 380B of jaw members 320A, 320B and a distal position within the distal ends 381A, 381B of jaw members 320A, 320B. In various embodiments, the distal portions 373A, 373B of the fluid circuits 370A, 370B can extend distally with respect to the distal-most position of the cutting member 340. In other embodiments, the distal portions 373A, 373B of the fluid circuits 370A, 370B can be aligned with the distal-most position of the cutting member 340 or positioned proximally with respect to the distal-most position of the cutting member 340.

In various embodiments, further to the above, the first conduit 371A can be sealed such that fluid flowing through the first fluid-conveying circuit 370A does not escape therefrom. Similarly, the second conduit 371B can be sealed such that fluid flowing through the second fluid-conveying circuit 370B does not escape therefrom. In certain embodiments, the conduits 371A and 371B can each comprise one or more tubular members having an aperture therein wherein the jaw bodies 321A, 321B of jaw members 320A, 320B can be formed around the conduits 371A, 371B such that at least a portion of the conduits 371A, 371B are embedded within the jaw bodies 371A, 371B. In at least one such embodiment, the jaw bodies 321A, 321B can be comprised of plastic and can be injection molded around the conduits 371A, 371B which can be comprised of brass tubes, for example. In various embodiments, each of the jaw bodies 321A, 321B can comprise one or more apertures extending therethrough wherein the conduits 371A, 371B can be inserted into the apertures. In at least one such embodiment, the conduits 371A, 371B can be sufficiently flexible such that they can resiliently bend and navigate curves in the apertures while, at the same time, the conduits 371A, 371B can be sufficiently stiff such that they can be inserted through the apertures. In various embodiments, at least one of the conduits 371A, 371B can be sufficiently flexible to accommodate the opening and closing of the jaw members 320A, 320B. In certain embodiments, the apertures in the jaw member bodies 321A, 321B can be sufficiently sealed such that fluid can be circulated through the apertures without conduits positioned therein. In any event, the surgical instrument can further comprise at least one fluid inlet, at least one fluid outlet, and at least one fluid manifold, wherein the manifold can be configured to distribute fluid from the fluid inlet into the conduits 371A and 371B and direct the fluid exiting the conduits 371A and 371B to the fluid outlet once the fluid has passed through the end effector. In at least one embodiment, the handle of the surgical instrument can comprise a fluid inlet and the shaft can comprise an inlet conduit extending between the fluid inlet and a fluid inlet manifold positioned in the shaft and/or the end effector of the surgical instrument. In at least one such embodiment, the first portions 372A, 372B of the fluid conduits 371A, 371B can be in fluid communication with the fluid inlet manifold such that fluid can flow from the fluid inlet, through the inlet conduit, and into the fluid conduits 371A, 371B, for example. As outlined above, the fluid can circulate through the fluid conduits 371A, 371B and, in various embodiments, the fluid can exit the conduits 371A, 371B via the second portions 374A, 374B and flow into a fluid outlet manifold positioned within the shaft and/or end effector. The outlet manifold can direct the fluid from the fluid-conveying circuits 370A and 370B into an outlet conduit in the shaft which can be in fluid communication with the fluid outlet.

Figure 8:
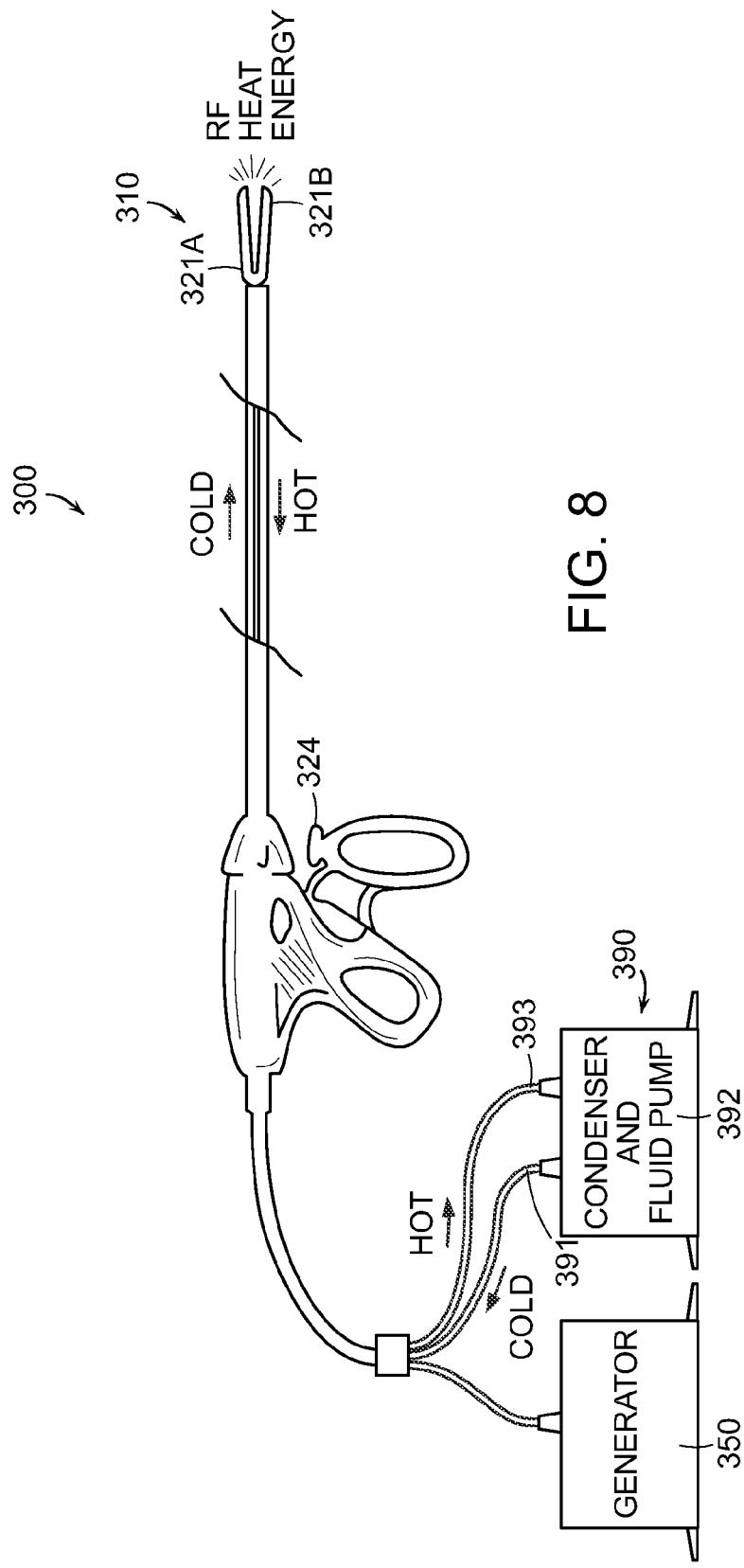
FIG. 8 illustrates a system for use with a surgical instrument comprising the end effector of FIG. 5 and/or the end effector of FIG. 7.

In various embodiments, the fluid inlet and the fluid outlet of a surgical instrument can be placed in fluid communication with an external circulatory system which can be configured to circulate fluid through the surgical instrument as described above. In at least one embodiment, referring now to FIG. 8, a surgical instrument 300 can be placed in fluid communication with a circulatory system 390 which can comprise a pump and condenser assembly 392, a supply conduit 391 in fluid communication with the fluid inlet of surgical instrument 300 and assembly 392, and a return conduit 393 in fluid communication with the fluid outlet of the surgical instrument 300 and assembly 392. In use, the pump can be actuated in order to pressurize fluid within the circulatory system 390 and discharge the pressurized fluid into supply conduit 391. The pressurized fluid can circulate through instrument 300 and end effector 310 and absorb heat therefrom. The heated fluid can then return to the pump and condenser assembly 392 via return conduit 393 wherein the pressure of the pressurized fluid can be reduced, such as by at least one throttle valve, for example, and heat can be extracted from the fluid via one or more condensers in order to cool the fluid such that the cooled fluid can be re-pressurized by the pump. In various embodiments, further to the above, surgical instrument 300 can further comprise a switch 324, for example, which can be configured to, one, electrically couple electrodes within the end effector 310 with generator 350, for example, and, two, activate the pump of the circulatory system 390. In at least one such embodiment, the fluid can be circulated at the same time that electrical energy is supplied to the electrodes of the surgical instrument. In certain embodiments, the surgical instrument 300 can comprise a controller which can be programmed to delay one of the application of energy to the electrodes and/or the circulation of fluid after the switch 324 has been actuated. More particularly, in at least one embodiment, the controller can be configured to initiate the circulation of fluid before the end effector electrodes are polarized while, in other circumstances, the controller can be configured to initiate the circulation of fluid after the electrodes are polarized. In certain other embodiments, the surgical instrument 300 can comprise two switches for independently operating the pump and the power supply.

In various embodiments, further to the above, the circulatory fluid can comprise any suitable working fluid, such as water, saline solution, and/or R-134a refrigerant, for example. In certain embodiments, the circulatory fluid can comprise chilled, super-cooled, and/or cryogenic, liquids, gasses, and/or gels, for example. In any event, the heat extracted from the circulatory fluid by the condenser of assembly 392 can be discharged into the surrounding atmosphere and/or utilized to warm fluids used for suction and/or irrigation, for example. In at least one embodiment, the condenser of assembly 392 can be in thermal communication with a reservoir of saline solution, wherein the warmed saline solution can be used to irrigate the tissue within the surgical site, for example. In certain embodiments, the saline solution system can comprise a conduit which extends into and/or is wrapped around assembly 392 which exposes the saline solution to the heat discharged by the condenser. In certain embodiments, the surgical site within the patient may be insufflated with carbon dioxide, for example, and, in various embodiments, the surgical instrument 300 can comprise one or more channels and/or conduits extending through the end effector 310 which can be configured to convey compressed carbon dioxide to the surgical site. In at least one such embodiment, such channels and/or conduits can comprise a first end which can be placed in fluid communication with a source of compressed carbon dioxide and, in addition, a second end which comprises an opening through which the carbon dioxide can exit the channels and/or conduits and enter into the surgical site. In various embodiments, the carbon dioxide flowing through the end effector may absorb heat from the electrodes within the end effector 310, for example. In at least one such embodiment, the handle of the surgical instrument 300 can further comprise an insufflation inlet which is in fluid communication with an insufflation conduit extending through the shaft and end effector of the surgical instrument. In various embodiments, the surgical instrument can comprise at least one insufflation conduit which extends through the first jaw 321A of the end effector 310 and at least one insufflation conduit which extends through the second jaw 321B of the end effector 310, for example. In at least one embodiment, the insufflation conduits extending through the shaft may be positioned adjacent to, positioned against, and/or wrapped around the outlet conduit of the fluid circulation system. In at least one embodiment, the carbon dioxide of the insufflation system can flow, in general, from the handle toward the end effector of the surgical instrument while the warmed fluid flowing through the outlet conduit can flow, in general, from the end effector toward the handle of the surgical instrument. In at least one such embodiment, the insufflation system can comprise a counter-flow heat exchanger with the circulatory system, for example. In certain embodiments, the outlet conduit of the fluid circulatory system can be positioned within and extend through at least a portion of the insufflation conduit.

In various embodiments, a surgical instrument can comprise a circulatory system including a pump and a reservoir. In at least one embodiment, the pump and the reservoir can be positioned within and/or attached to the handle of the surgical instrument. In lieu of a fluid inlet, the pump can be in fluid communication with the fluid reservoir and the fluid inlet conduit extending through the shaft such that fluid can be drawn from the fluid reservoir and expelled into the fluid inlet conduit. Furthermore, in lieu of a fluid outlet, the reservoir can be in fluid communication with the fluid outlet conduit extending through the shaft wherein fluid from the outlet conduit can be discharged into the reservoir. In various embodiments, the surgical instrument can further comprise means for cooling the fluid in the reservoir wherein such means can include a fan and/or a refrigeration circuit, for example.

In various embodiments, as discussed above, the fluid circulatory system extending through the end effector of the surgical instrument can be sealed such that fluid does not escape from the circulatory system. In certain other embodiments, the fluid circulatory system can be configured to release the circulating fluid onto the electrodes, the jaws supporting the electrodes, and/or the tissue positioned between and/or surrounding the jaws of the end effector, for example. In various embodiments, the fluid can be released before, during, and/or after the cutting member has been advanced through the tissue and/or before, during, and/or after the electrodes of the end effector have been polarized. In at least one embodiment, the cutting member can be configured to transect the tissue and rupture at least one of the fluid conduits. In at least one such embodiment, the cutting member can comprise an additional cutting edge configured to puncture and incise a fluid conduit as the cutting member is advanced. In certain embodiments, a surgical instrument can comprise an additional cutting member which can be selectively advanced in order to rupture the fluid conduits independently of the advancement of the tissue cutting member. In at least one such embodiment, the handle of the surgical instrument can comprise an additional actuator, or trigger, operably coupled with the additional cutting member in order to advance the additional cutting member distally and retract the additional cutting member proximally.

In at least one embodiment, the fluid conduits extending through the jaws can be comprised of a meltable material which can be configured to melt during the use of the surgical instrument. In at least one such embodiment, the fluid conduits can be, one, sealed when the temperature of the material comprising the fluid conduits is below its melting temperature and, two, configured to rupture once the temperature of the material comprising the fluid conduits reaches and/or exceeds its melting temperature, for example. In at least one such embodiment, the material comprising the fluid conduits can be selected such that the fluid flowing through the conduits may not be dispensed onto the tissue until the tissue has been at least partially treated by the current flowing through the polarized electrodes. In certain embodiments, further to the above, the fluid conduits can be configured to rupture at a predetermined temperature, such as approximately 90 degrees Celsius, approximately 100 degrees Celsius, approximately 110 degrees Celsius, approximately 120 degrees Celsius, and/or approximately 130 degrees Celsius, for example.

Figure 6:
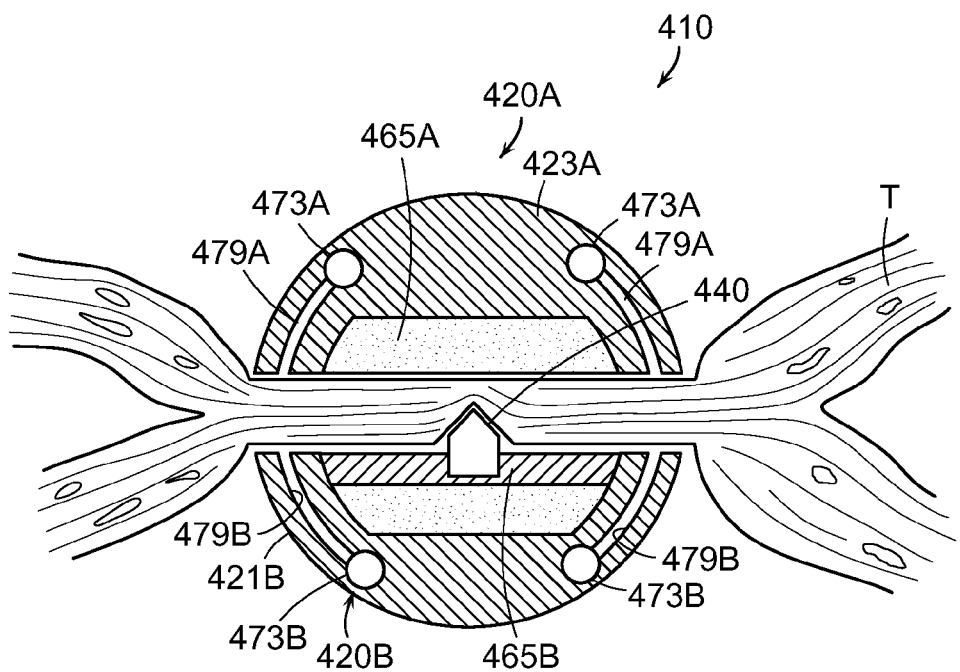
FIG. 6 is a cross-sectional view of an alternative embodiment of an end effector comprising fluid-conveying conduits extending through first and second jaws of the end effector.
Figure 7:
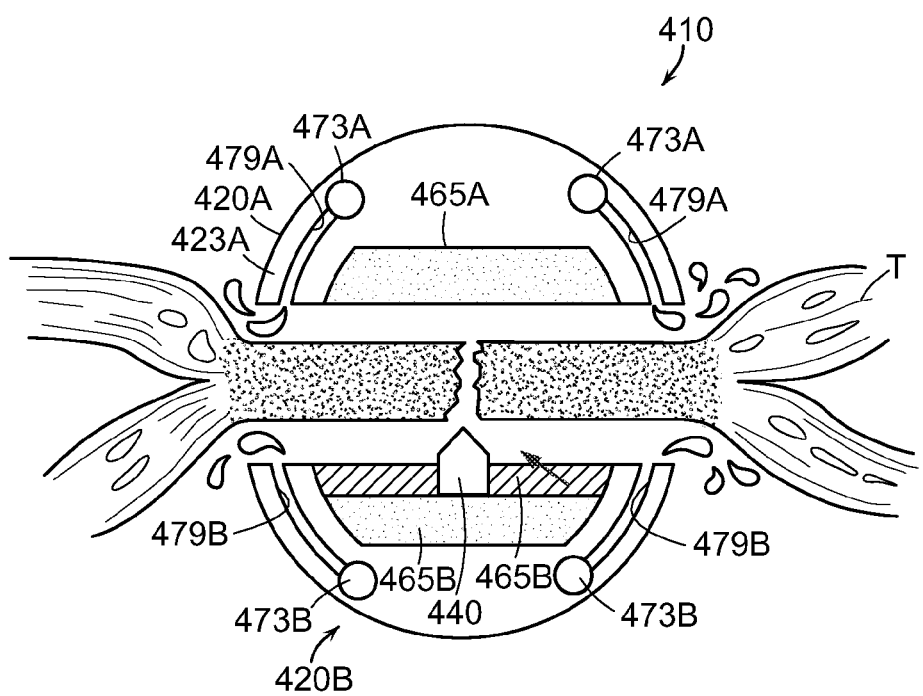
FIG. 7 is another cross-sectional view of the end effector of FIG. 6 illustrated with the fluid-conveying conduits after they have been ruptured.

In various embodiments, the circulatory fluid dispensed onto the tissue can comprise one or more cellular growth factors, hemostatic agents, and/or tissue sealants, for example. In at least one such embodiment, a biocompatible heat-activated tissue sealant, such as albumin, fibrogen, and/or cyanoacrylates, for example, could be dispensed from the fluid circulatory system before, during, and/or after the cutting member, such as cutting member 340, for example, is advanced and/or before, during, and/or after the electrodes of the end effector have been polarized. In certain embodiments, the release of the fluid from the circulatory system conduits can be actuated independently of the advancement of cutting member 340 and/or the polarization of the electrodes. In at least one embodiment, referring now to FIGS. 6 and 7, the fluid-conveying conduits 473A and 473B extending through jaws 420A and 420B, respectively, of end effector 410 can be ruptured by the fluid pressure of the fluid flowing through the circulatory system. More particularly, in at least one embodiment, the pump can be configured to pressurize the circulatory fluid to a first pressure in order to circulate the fluid through the conduits 473A and 473B and cool the tissue T positioned intermediate the electrodes 465A and 465B of end effector 410 and, in addition, a second pressure which is larger than the first pressure in order to burst at least a portion of the conduits 473A and 473B and release the circulatory fluid as illustrated in FIG. 7. In various embodiments, the jaw body 423A of first jaw 420A can comprise one or more channels 479A extending between the conduits 473A and a tissue-contacting surface of the first jaw 420A which can be configured to direct the released fluid onto the tissue. Similarly, the jaw body 423B of first jaw 420B can comprise one or more channels 479B extending between the conduits 473B and a tissue-contacting surface of the second jaw 420B which can also be configured to direct the released fluid onto the tissue. In at least one such embodiment, the channels 479B can comprise outlets positioned adjacent to the outer perimeter of the jaws such that the fluid, when dispensed, can inhibit the lateral spread of heat from the end effector.

In various embodiments, a surgical instrument can comprise a controller, or computer, in signal communication with the pump, wherein the controller can be configured to instruct the pump to pressurize the fluid to the first, or operating, pressure and the second, or rupture, pressure. In certain embodiments, the surgical instrument can further comprise one or more temperature sensors in the end effector which can be in signal communication with the controller. In various embodiments, a sensor can be in signal communication with the controller via a wired and/or wireless connection. In use, the controller can instruct the pump to increase the fluid pressure from the operating pressure to the rupture pressure when the controller has determined that the electrodes of the end effector, and/or the tissue positioned between the electrodes, have met or exceeded a predetermined, or threshold, temperature, for example. In certain embodiments, the surgical instrument can comprise a position sensor, such as a proximity sensor, for example, configured to detect when the cutting member, such as cutting member 440, for example, has reached its distal-most position. The position sensor can be in signal communication with the controller such that, when the position sensor has detected that the cutting member 440 is in its distal-most position, the controller can instruct the pump to increase the fluid pressure from the operating pressure to the rupture pressure. In certain embodiments, the surgical instrument can comprise a plurality of sensors, such as a plurality of proximity sensors arranged in a longitudinal array, for example, which can be configured to detect when the cutting member is being retracted, i.e., moved proximally away from the distal end of the end effector. These sensors can be in signal communication with the controller such that, when the sensors have detected that the cutting member is being retracted, the controller can instruct the pump to increase the fluid pressure from the operating pressure to the rupture pressure. In certain embodiments, the surgical instrument can comprise a sensor, such as a Hall effect sensor, for example, which can be configured to detect when the first jaw 420A, for example, is being moved from a closed position to an open position. This sensor can be in signal communication with the controller such that, when the sensor has detected that the first jaw 420A is opening, the controller can instruct the pump to increase the fluid pressure from the operating pressure to the rupture pressure.

In various embodiments, a surgical instrument can comprise a fluid conveying circuit including one or more conduits having at least one discharge port therein. In at least one embodiment, the configuration of the discharge port can change during use. For example, the discharge port can comprise a first configuration when the pressure of the fluid circulating through the fluid conduits is at a first pressure and a second configuration when the pressure of the fluid is at a second pressure. In at least one such embodiment, the discharge port can be, one, closed and/or sealed when the fluid is circulated through the fluid conveying circuit at the first pressure and, two, opened when the pressure of the fluid is increased to the second pressure. After the discharge port has been at least partially opened owing to the elevated fluid pressure, the fluid can flow through the aperture and onto the tissue being treated, for example. In at least one such embodiment, the fluid conduit, or at least the portion of the fluid conduit surrounding the discharge port, can be comprised of a flexible material which can be configured to allow the fluid conduit, and the discharge port, to expand when the pressure of the fluid is increased. In various embodiments, the discharge port can comprise an aperture which can be configured to expand between a first diameter and a second diameter, for example, when the pressure of the fluid is increased between the first pressure and the second pressure. In at least one such embodiment, the discharge port may not be completely sealed in its first configuration and, as a result, a quantity of fluid can be configured to flow through the discharge port in its first configuration and its second configuration, although at different rates. For example, the first configuration of the discharge port can permit a first mass flow rate of circulatory fluid to be discharged therethrough and the second configuration of the discharge port can permit a second mass flow rate of circulatory fluid to be discharged therethrough. In various embodiments, the discharge port can be larger in its second configuration than its first configuration and, as a result, the second mass flow rate can be larger than the first mass flow rate.

In various embodiments, further to the above, the fluid circulatory system can comprise a plurality of discharge ports in fluid communication within one or more conduits. In at least one embodiment, each discharge port can comprise a hole which can permit fluid to flow therethrough with a variable mass flow rate. In at least one such embodiment, the mass flow rate of the fluid flowing through the discharge ports can be a function of the fluid pressure. In use, the fluid pressure can be modulated upwardly in order to increase the mass flow rate of the fluid flowing through the discharge ports and, also, downwardly in order to decrease the mass flow rate of the fluid flowing through the discharge ports. In use, the fluid pressure can be modulated between a plurality of pressures, including three or more pressures, for example, in order to produce three or more mass flow rates, for example. In various embodiments, the mass flow rate of the fluid flowing through the discharge ports can be directly proportional to the fluid pressure and can increase and/or decrease linearly, at least substantially linearly, and/or geometrically, for example, in response to changes in the fluid pressure. In certain embodiments, the conduits of the fluid circulatory system can comprise one or more first discharge ports which can be configured to permit a first mass flow rate of the fluid to flow therethrough for a given fluid pressure and one or more second discharge ports configured to permit a second mass flow rate of fluid to flow therethrough for the given fluid pressure. In at least one embodiment, the conduits can comprise any suitable number and/or type of discharge ports having different configurations positioned within the end effector of the electrosurgical instrument. In certain embodiments, a surgical instrument can comprise two or more separate circulatory systems which can be operated at different pressures in order to provide an adjustable, sequentially-activated, and/or sequentially-deactivated, discharge of fluid onto the end effector and/or tissue being treated. In at least one such embodiment, the instrument can comprise a first circulatory system configured to release a fluid at a first fluid pressure and a second circulatory system configured to release a fluid at a second fluid pressure. In various embodiments, the fluid within the first circulatory system can be the same as the fluid within the second circulatory system or it can be different.

In various embodiments, further the above, the fluid circulatory system can comprise one or more holes within one or more fluid conduits which can be configured such that they, one, do not leak, or do not appreciably leak, below a certain fluid pressure of the fluid and, two, begin to weep and/or spray at or above the certain fluid pressure. In certain embodiments, the conduits can be comprised of a resilient material, for example, which can be configured to allow the holes to return, or at least substantially return, to their original shape after the fluid pressure has dropped below the certain pressure in order to substantially close and/or seal the holes once again. In at least one such embodiment, the instrument can be reset after fluid has been dispensed from the circulatory system such that the fluid can be selectively dispensed from the circulatory system once again by increasing the fluid pressure above the certain pressure.

In various embodiments, as described above, current can flow from one electrode to another while passing through the tissue captured by the end effector of the surgical instrument. As also described above, the current passing through the tissue can heat the tissue. In various circumstances, however, the tissue may become overheated. In order to avoid such overheating, the electrodes of various surgical instruments can comprise materials which may no longer conduct current, or may conduct at least substantially less current, when the electrode materials have reached or exceeded a certain temperature. Stated another way, in at least one embodiment, the electrical resistance of the electrode material can increase with the temperature of the material and, in certain embodiments, the electrical resistance of the material can increase significantly when the material has reached or exceeded a certain transition, or switching, temperature. In various circumstances, such materials can be referred to as positive temperature coefficient, or PTC, materials. In at least some such PTC materials, the PTC material can be comprised of a first non-conductive material, or substrate, which has a high electrical resistance and, in addition, a second, conductive material, or particles, having a lower electrical resistance interdispersed throughout the substrate material. In at least one embodiment, the substrate material can comprise polyethylene and/or high-density polyethylene (HDPE), for example, and the conductive material can comprise carbon particles, for example. In any event, when the temperature of the PTC material is below its transition temperature, the conductive material can be present in the non-conductive material in a sufficient volumetric density such that the current can flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

Further to the above, describing a material as having a positive temperature coefficient of resistance (PTC) can mean that the resistance of the material increases as the temperature of the material increases. Many metal-like materials exhibit electrical conduction that has a slight positive temperature coefficient of resistance. In such metal-like materials, the PTC's variable resistance effect is characterized by a gradual increase in resistance that is linearly proportional to temperature—that is, a linear PTC effect. A "nonlinear" PTC effect can be exhibited by certain types of polymer matrices, or substrates, that are doped with conductive particles. These polymer PTC compositions can comprise a base polymer that undergoes a phase change or can comprise a glass transition temperature Tg such that the PTC composition has a resistance that increases sharply over a narrow temperature range.

Polymeric PTC material can consist of a crystalline or semi-crystalline polymer (e.g., polyethylene) that carries a dispersed filler of conductive particles, such as carbon powder or nickel particles, for example, therein. In use, a polymeric PTC material can exhibit temperature-induced changes in the base polymer in order to alter the electrical resistance of the polymer-particle composite. In a low temperature state, the crystalline structure of the base polymer can cause dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes $I^2R$ heating (Joule heating) within the PTC material, the polymer base material may be elevated in temperature until it exceeds a phase transformation temperature. As the polymer passes through this phase transformation temperature, the crystalline structure can change to an amorphous state. The amorphous state can cause the conductive particles to move apart from each other until the carbon chains are disrupted and can no longer conduct current. Thus, the resistance of the PTC material increases sharply. In general, the temperature at which the base polymer transitions to its amorphous state and affects conductivity is called its switching temperature Ts. In at least one embodiment, the transition or switching temperature Ts can be approximately 120 degrees Celsius, for example. In any event, as long as the base polymer of the PTC material stays above its switching temperature Ts, whether from external heating or from an overcurrent, the high resistance state will remain. Reversing the phase transformation allows the conductive particle chains to reform as the polymer re-crystallizes to thereby restore multiple current paths, and a low resistance, through the PTC material. Conductive polymer PTC compositions and their use are disclosed in U.S. Pat. Nos. 4,237,441; 4,304,987; 4,545,926; 4,849,133; 4,910,389; 5,106,538; and 5,880,668, the entire disclosures of which are incorporated by reference herein.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a handle;
   a conductor configured to be electrically coupled to a power source;
   an end effector, comprising:
      a first jaw;
      a second jaw, wherein one of said first jaw and said second jaw is movable relative to the other of said first jaw and said second jaw between an open position and a closed position to capture tissue therebetween; and
      a first electrode electrically coupled with said conductor;
   a fluid conveying circuit at least partially embedded within said first jaw, comprising:
      a first fluid passage; and
      a second fluid passage; and
   a pump configured to circulate a fluid through said fluid conveying circuit, wherein said pump is configured to pressurize said fluid to a first fluid pressure and a second fluid pressure, wherein said second fluid pressure is higher than said first fluid pressure, and wherein at least one of said first passage and said second passage is configured to burst when the fluid is pressurized to said second fluid pressure.

2. The surgical instrument of claim 1, wherein said end effector comprises a proximal end and a distal end opposite said proximal end, wherein said surgical instrument further comprises:
   a cutting member movable between a proximal position within said proximal end of said end effector and a distal position within said distal end of said end effector;
   a sensor configured to detect the movement of said cutting member into said distal position; and
   a controller operably coupled with said sensor and said pump, wherein said controller is programmed to operate said pump to generate said second fluid pressure when said sensor communicates to said controller that said cutting member is in said distal position.

3. A surgical instrument, comprising:
   a handle;
   a conductor configured to be electrically coupled to a power source;
   an end effector, comprising:
      a first law;
      a second jaw, wherein one of said first law and said second jaw is movable relative to the other of said first jaw and said second jaw between an open position and a closed position to capture tissue therebetween; and
      an electrode electrically coupled with said conductor; and a fluid conveying circuit at least partially embedded within said first jaw, comprising:
a first fluid passage; and
a second fluid passage,
wherein at least one of said first fluid passage and said second fluid passage is configured to rupture such that fluid flowing through said fluid conveying circuit can flow onto the tissue captured between said first jaw and said second jaw.

4. The surgical instrument of claim 3, wherein said fluid comprises at least one cellular growth factor.

5. The surgical instrument of claim 3, wherein said fluid comprises at least one hemostatic agent.

6. The surgical instrument of claim 3, wherein said fluid comprises at least one heat-activated tissue sealant.

7. The surgical instrument of claim 3, wherein said first passage comprises a first conduit configured to melt and rupture owing to heat generated by said electrode.

8. A surgical instrument, comprising:
a handle;
a conductor configured to be electrically coupled to a power source;
an end effector, comprising:
a first jaw;
a second jaw, wherein one of said first jaw and said second jaw is movable relative to the other of said first jaw and said second jaw between an open position and a closed position to capture tissue therebetween;
a first electrode electrically coupled with said conductor; and
a second electrode;
a fluid conveying circuit at least partially embedded within said first jaw; and
a cutting member configured to be moved relative to said first electrode and said second electrode and incise said fluid conveying circuit.

9. A surgical instrument, comprising:
a handle;
a conductor configured to be electrically coupled to a power source;
an end effector, comprising:
a first jaw;
a second jaw, wherein one of said first jaw and said second jaw is movable relative to the other of said first jaw and said second jaw between an open position and a closed position to capture tissue therebetween; and
an electrode electrically coupled with said conductor; and
a fluid conveying circuit at least partially embedded within said first jaw, comprising:
a first fluid passage; and
a second fluid passage,
wherein at least one of said first fluid passage and said second fluid passage comprises a discharge port therein, and wherein said discharge port is expandable between a first configuration when fluid in said fluid conveying circuit is pressurized at a first fluid pressure and a second configuration when fluid in said fluid conveying circuit is pressurized at a second fluid pressure.

10. The surgical instrument of claim 9, wherein said discharge port is sealed when said discharge port is in said first configuration such that the fluid in said fluid conveying circuit cannot flow through said discharge port, and wherein the fluid can flow through said discharge port when said discharge port is in said second configuration.

11. A surgical instrument, comprising:
a handle comprising a trigger and a switch;
a shaft extending from said handle, wherein said shaft comprises:
a conductor configured to be electrically coupled with a power source upon an actuation of said switch; and
a drive member operably coupled with said trigger;
an end effector extending from said shaft, comprising:
a first jaw;
a second jaw, wherein one of said first jaw and said second jaw is movable relative to the other of said first jaw and said second jaw between an open position and a closed position to capture tissue therebetween; and
an electrode electrically coupled with said conductor;
a fluid conveying circuit;
a pump configured to circulate a fluid through said fluid conveying circuit, wherein said pump is configured to pressurize said fluid to a first fluid pressure and a second fluid pressure, wherein said second fluid pressure is higher than said first fluid pressure, and wherein said fluid conveying circuit is configured to burst when the fluid is pressurized to said second fluid pressure.

12. The surgical instrument of claim 11, wherein said surgical instrument further comprises:
a cutting member operably coupled with said drive member, wherein an actuation of said trigger is configured to move said cutting member between a proximal position and a distal position;
a sensor configured to detect the movement of said cutting member into said distal position; and
a controller operably coupled with said sensor and said pump, wherein said controller is programmed to operate said pump to generate said second fluid pressure when said sensor communicates to said controller that said cutting member is in said distal position.

13. A surgical instrument, comprising:
a handle comprising a trigger and a switch;
a shaft extending from said handle, wherein said shaft comprises:
a conductor configured to be electrically coupled with a power source upon an actuation of said switch; and
a drive member operably coupled with said trigger;
an end effector extending from said shaft, comprising:
a first jaw;
a second jaw, wherein one of said first jaw and said second jaw is movable relative to the other of said first jaw and said second jaw between an open position and a closed position to capture tissue therebetween;
an electrode electrically coupled with said conductor;
a fluid conveying circuit,
wherein said fluid conveying circuit is configured to rupture such that fluid flowing through said fluid conveying circuit can flow onto the tissue captured between said first jaw and said second jaw.

14. The surgical instrument of claim 13, wherein said fluid comprises at least one cellular growth factor.

15. The surgical instrument of claim 13, wherein said fluid comprises at least one hemostatic agent.

16. The surgical instrument of claim 13, wherein said fluid comprises at least one heat-activated tissue sealant.

17. The surgical instrument of claim 13, wherein said fluid conveying circuit comprises a conduit configured to melt and rupture owing to heat generated by said electrode.

18. A surgical instrument, comprising:
a handle comprising a trigger and a switch;
a shaft extending from said handle, wherein said shaft comprises:

a conductor configured to be electrically coupled with a power source upon an actuation of said switch; and
a drive member operably coupled with said trigger;
an end effector extending from said shaft, comprising:
a first jaw;
a second jaw, wherein one of said first jaw and said second jaw is movable relative to the other of said first jaw and said second jaw between an open position and a closed position to capture tissue therebetween;
a first electrode electrically coupled with said conductor; and
a second electrode;
a fluid conveying circuit; and
a cutting member configured to be moved relative to said first electrode and said second electrode and incise said fluid conveying circuit.

19. A surgical instrument, comprising:
a handle comprising a trigger and a switch;
a shaft extending from said handle, wherein said shaft comprises:
a conductor configured to be electrically coupled with a power source upon an actuation of said switch; and
a drive member operably coupled with said trigger;
an end effector extending from said shaft, comprising:
a first jaw;
a second jaw, wherein one of said first law and said second jaw is movable relative to the other of said first jaw and said second jaw between an open position and a closed position to capture tissue therebetween; and
an electrode electrically coupled with said conductor; and
a fluid conveying circuit,
wherein said fluid conveying circuit comprises a discharge port therein, and wherein said discharge port is expandable between a first configuration when fluid in said fluid conveying circuit is pressurized at a first fluid pressure and a second configuration when fluid in said fluid conveying circuit is pressurized at a second fluid pressure.

20. The surgical instrument of claim 19, wherein said discharge port is sealed when said discharge port is in said first configuration such that the fluid in said fluid conveying circuit cannot flow through said discharge port, and wherein the fluid can flow through said discharge port when said discharge port is in said second configuration.

21. A surgical instrument for treating tissue, comprising:
a conductor configured to be electrically coupled to a power source;
an end effector, comprising:
a first jaw; and
a second jaw,
an electrode electrically coupled with said conductor; and
a fluid conveying circuit comprising means for releasing fluid from within said fluid conveying circuit onto the tissue.

22. A surgical instrument, comprising:
a handle;
an end effector, comprising:
a first jaw; and
a second jaw, wherein one of said first jaw and said second jaw is movable relative to the other of said first jaw and said second jaw between a first position and a second position to capture tissue therebetween; and
a fluid conveying circuit, wherein said fluid conveying circuit is adjustable between a first condition and an open condition, wherein fluid flowing through said fluid conveying circuit can be expelled onto the tissue when said fluid conveying circuit is in said open condition.

23. A surgical instrument, comprising:
a handle;
an end effector, comprising:
a first jaw;
a second jaw, wherein one of said first jaw and said second jaw is movable relative to the other of said first jaw and said second jaw between a first position and a second position to capture tissue therebetween; and
a fluid conveying circuit; and
a cutting member configured to be moved relative to said first jaw and said second jaw and incise said fluid conveying circuit.

\* \* \* \* \*